United States Patent
Triebel et al.

(10) Patent No.: US 8,118,806 B2
(45) Date of Patent: Feb. 21, 2012

(54) EYE-CONTACT ELEMENT

(75) Inventors: Peter Triebel, Jena (DE); Olaf Kittelmann, Berlin (DE); Klaus Vogler, Eckental (DE)

(73) Assignee: Wavelight AG, Erlangen (DE)

( * ) Notice: Subject to any disclaimer, the term of this patent is extended or adjusted under 35 U.S.C. 154(b) by 236 days.

(21) Appl. No.: 11/771,949

(22) Filed: Jun. 29, 2007

(65) Prior Publication Data
US 2008/0228176 A1    Sep. 18, 2008

(30) Foreign Application Priority Data
Jul. 4, 2006    (EP) .................................. 06013828

(51) Int. Cl.
*A61B 18/18* (2006.01)
(52) U.S. Cl. ................. 606/5; 606/4; 128/898
(58) Field of Classification Search .................. None
See application file for complete search history.

(56) References Cited

U.S. PATENT DOCUMENTS

| | | | |
|---|---|---|---|
| 5,549,632 A * | 8/1996 | Lai | 606/5 |
| 6,325,792 B1 | 12/2001 | Swinger et al. | |
| 6,342,053 B1 | 1/2002 | Berry | |
| 6,623,476 B2 | 9/2003 | Juhasz et al. | |
| 6,730,074 B2 | 5/2004 | Bille et al. | |
| 6,899,707 B2 * | 5/2005 | Scholler et al. | 606/5 |
| 6,999,707 B2 | 2/2006 | Okamura | |
| 2002/0103481 A1 * | 8/2002 | Webb et al. | 606/5 |
| 2002/0103482 A1 * | 8/2002 | Scholler et al. | 606/5 |
| 2004/0070761 A1 | 4/2004 | Horvath et al. | |

FOREIGN PATENT DOCUMENTS

| | | |
|---|---|---|
| EP | 1034755 | 9/2000 |
| EP | 1034757 | 9/2000 |
| WO | 03/002008 | 1/2003 |
| WO | 2005/079717 | 9/2005 |

OTHER PUBLICATIONS

Glass Dynamics, LLC, "Refractive Index for BK7 and Fused Silica".*

* cited by examiner

*Primary Examiner* — Henry M Johnson, III
*Assistant Examiner* — Lynsey Crandall
(74) *Attorney, Agent, or Firm* — Haynes and Boone, LLP

(57) ABSTRACT

An optical eye-contact element is disclosed that is at least partly translucent, the optical eye-contact element giving rise to a wavefront error of at most about $\lambda/2$, preferentially at most about $\lambda/4$, highly preferentially at most about $\lambda/10$, in a traversing light beam. The optical eye-contact element may be a so-called applanation plate or applanation lens.

20 Claims, 2 Drawing Sheets

EYE-CONTACT ELEMENT

Figure 1:
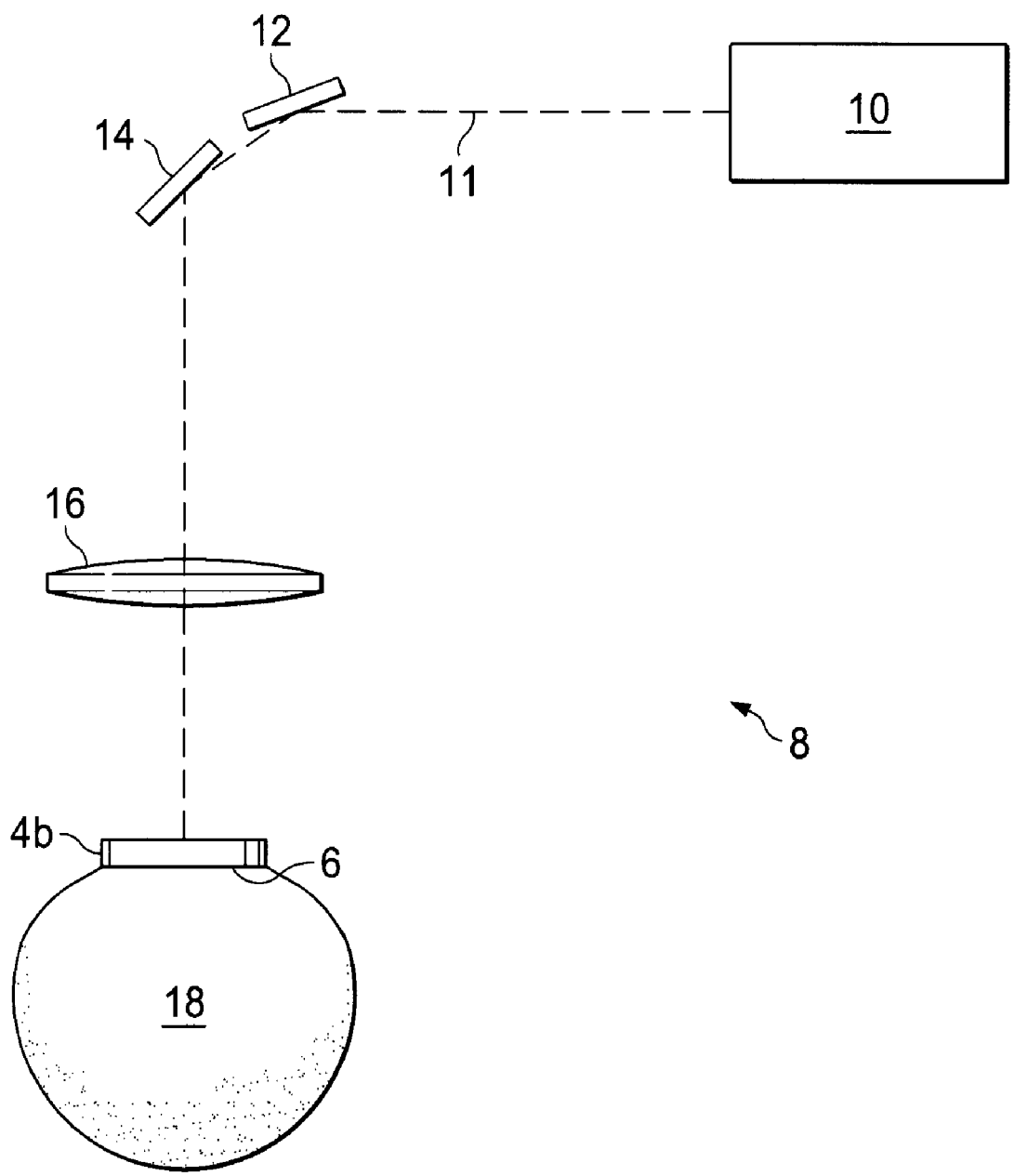

This patent application claims priority to European Patent Application No. 06 013 828.6 filed 4 Jul. 2006, the entirety of which is incorporated by reference herein.

The invention relates to an improved applanation lens or applanation plate for an ophthalmological operation.

Pulsed laser radiation is used in ophthalmic surgery, for example, for the purpose of placing incisions in the cornea or for the purpose of ablating tissue from the cornea. The laser radiation that is beamed in brings about a photodisruptive process in the corneal tissue which results in the separation of tissue or in the removal of tissue material. Such treatments of the cornea, take place, for example, within the scope of refractive processes for diminishing or totally remedying conditions of defective vision of the eye, in the course of which the cornea is reshaped and, by this means, its refractive properties are changed.

The dominant refractive process of corneal surgery is the so-called LASIK process (laser in-situ keratomileusis). In this case a small cover is cut out of the cornea, either mechanically (by means of an oscillating cutting blade in a so-called microkeratome) or optically (by means of laser radiation—for example, so-called femtosecond laser systems), said cover being still attached to the cornea by a part of its edge. Subsequently this cover—which is customarily also designated as a flap—is folded to one side, as a result of which the stroma situated underneath it becomes accessible. Stromatous tissue is then ablated with laser radiation in accordance with an ablation profile that has been ascertained for the particular 3D patient. The cover is then folded back again, as a result of which the wound is able to heal relatively quickly and the improved visual capacity is attained within an extremely short time.

A femtosecond laser microkeratome comprises a femtosecond laser source, a scanner, which deflects the laser beam of the femtosecond laser source successively over a treatment region, focusing optics, and an applanation plate or applanation lens which is arranged on the cornea of the eye. A system of such a type is described in U.S. Pat. No. 5,549,632, for example.

When a femtosecond microkeratome is employed, the LASIK incision in the cornea is produced by means of an almost planar juxtaposition of a plurality of photomicrodisruptions in the stroma of the cornea. The photomicrodisruptions are produced by femtosecond laser pulses which arise as a result of very high intensities (I>$10^{11}$ W/cm$^2$) femtosecond laser beam which is generated by a femtosecond laser source, and which are guided to the cornea by a suitably dimensioned optical beam path with path-folding mirrors, with an expanding telescope, with a high-speed scanner and with a high-precision, short-focal-length focusing objective with a sufficiently high numerical aperture (NA>0.20).

In order to obtain a precise LASIK incision with these femtosecond pulses, the spatial location of a region of focus of the femtosecond pulse in the tissue of the cornea has to be determined with a precision of about 5 μm in all three directions in space. The size of the region of focus and the location of the region of focus of the consecutive pulses of the femtosecond laser radiation also have to attain the predetermined values and positions within a precision of the same order of magnitude, i.e. about 5 μm in order to obtain a reliable and high-quality LASIK incision with a femtosecond laser system.

For good therapeutic success, a diameter d of the region of focus is required that is as small as possible, in order to obtain a reliable laser-induced optical breakdown (LIOB) with a laser energy E that is as low as possible at a defined fluence, i.e. energy density F (F=E/A). In this case the threshold for a laser-induced optical breakdown is already reliably exceeded at a low laser-pulse energy. As a result, damage to the cornea and to the iris by virtue of excessively energetic and powerful femtosecond laser pulses can be avoided.

For a laser-induced optical breakdown, a fluence from about 2 J/cm$^2$ to about 3 J/cm$^2$ is required. In addition, small, closely adjacent photomicrodisruptions located at precisely the same depth (diameter of the region of focus $d_F$) provide the best quality of incision, i.e. the lowest roughness, in the case of the femtosecond LASIK process. In this connection, the exceeding of the LIOB threshold is necessary:

$$F = \frac{E}{A} = \frac{E}{0.25\pi d_F^2} \geq F_{th} \approx 2 \ldots 3 \text{ J/cm}^2$$

It will be discerned that the fluence is inversely proportional to the square of the focal diameter, and consequently in the case of a smaller diameter of the region of focus the fluence will be greater—also at a low laser-pulse energy E—than the threshold $F_{th}$ for a laser-induced optical breakdown.

Theoretically, a femtosecond laser pulse can, at best, be focused to a value of the order of magnitude of the diameter $d_A$ of the Airy function. It holds that:

$$d_A \approx 2.44 \frac{\lambda}{D} f$$

from which, at best, the ideal laser quality $d_F \approx d_A$ follows:

$$d_A \approx d_F \approx 2.44 \frac{\lambda}{D} f$$

where f is the focal length of the focusing objective, λ is the wavelength of the femtosecond laser radiation, and D is the aperture or the diameter of the laser beam on the focusing lens.

However, this presupposes an almost perfect laser beam (in the fundamental mode or in a plane wave) and a diffraction-limited focusing by means of an aberration-free objective of focal length f.

Stringent demands therefore have to be made upon the optical quality of the structural elements of the entire optical beam path that the femtosecond laser radiation traverses. In addition to a high total transmission, which minimises the energy loss of the femtosecond pulses on the way to the treatment site—i.e. the eye or, to be more exact, the cornea—this makes stringent demands, in particular, upon the freedom from aberration of the optical components that are used. In addition, a deformation of the wavefront of the laser radiation that is as low as possible is required. This is typically expressed by the planarity, the homogeneity and the distortion-free optical guidance of the femtosecond laser beam in the form of fractions of the wavelength, for example λ/n. It goes without saying that the most expensive and most elaborate optical components of the femtosecond laser-beam path—for example, the expanding telescope and the focusing objective—are specified with this high degree of freedom from aberration. But the path-folding mirrors that are used in the beam path and also the deflecting mirrors that are employed in the scanner also have to satisfy the requirements as regards a high planarity and a low deformation of the wavefront of the femtosecond laser pulse.

A wavefront that has been deformed by an arbitrary optical element cannot readily be corrected by means of another optical element, and prevents the desired optimal, i.e. 'sharp', focusing, which in the case of a deformed waterfront also cannot be obtained with high-quality focusing optics.

In the course of the femtosecond LASIK process, so-called suction-ring holding devices are customarily used by way of interface with the eye of the patient, which are attached by suction onto the eye of the patient by means of a reduced pressure. As a result, the eye is coupled with an apparatus that includes a contact glass—for example, a so-called applanation plate or applanation lens—which comes into contact with the cornea. As a result, the eye is located in a defined position with respect to the focusing objective of the femtosecond laser beam.

It is further to be observed that the contact glass constitutes is a reference plane with respect to which the position of focus of the femtosecond laser beams can be oriented. This orientation is especially important for the Z-direction, i.e. for the location of the depth of focus on the other side of the contact glass in the cornea, in order to foe able to implement a LASIK incision to precisely the desired depth—for example, about 120 μm—with a corresponding depth precision of less than ±10 μm, as described in U.S. Pat. No. 6,899,707 B2, for example.

The contact glass that is used may be of spherical or plane design, A contact glass taking the form of a planar applanation plate facilitates the maintenance of a uniform depth of focus of the femtosecond laser beam, but by virtue of the applanation of the corneal curvature it increases the ocular pressure distinctly more severely, i.e. by more than about 100 mm Hg (0.133 bar), than a contact glass taking the form of a spherically curved applanation lens, which simulates the natural curvature of the cornea more or less well, though this entails a greater effort for the control of the uniform depth of focus, for example by means of a rapid shift of the focal length of the focusing objective in the Z-axis.

U.S. Pat. No. 6,899,707 B2 describes an applanation lens with a transmission of more than 90% within a wavelength range from 275 nm to 2500 nm. U.S. Pat. No. 6,730,074 B2 proposes a contact lens, the curvature of which corresponds to the corneal curvature. During the LASIK treatment, the point of focus is shifted in the Z-direction, in order to compensate the curvature effects. U.S. Pat. No. 6,342,053 B1 proposes a transparent shaping device coupled to the eye of a patient. The radius of curvature of the transparent shaping device corresponds approximately to the desired emmetropic shape of the anterior region of the cornea. During a heating process, for example by means of infrared radiation, the cornea is reshaped, and the new shape of the cornea corresponds to the curvature of the region of the transparent shaping device facing towards the eye.

Further examples of contact glasses, i.e. applanation plates or applanation lenses, are to be found in BP 1 034 755 A1, EP 1 034 757 A, U.S. Pat. No. 6,623,476 B2, U.S. Pat. No. 6,999,707 B2, U.S. Pat. No. 5,549,632 and WO 2005/079717 A1.

It is an object of the invention to improve the quality of a LASIK incision.

The object is achieved by means of an optical eye-contact element that is at least partly translucent, the optical eye-contact element giving rise to a wavefront error of at most about λ/2, preferentially at most about λ/4, highly preferentially at most about λ/10, in a traversing light beam. The so optical eye-contact element may be a so-called applanation plate or applanation lens. The optical eye-contact element may consist of a material or materials that give(s) rise to a wavefront error of at most about λ/2, preferentially at most about λ/4, highly preferentially at most about λ/10, in a traversing light beam.

In order to obtain a reliable incision with at femtosecond laser microkeratome, stringent demands are made upon the beam quality of a femtosecond laser source, of focusing optics and of expanding optics that the femtosecond laser radiation traverses. However, a person skilled in the art has not hitherto included the last but not insignificant element in the optical beam path, i.e. the eye-contact element, in the optical quality inspection. It is self-evident that this relatively simple element is still aisle to impair the wavefront quality—previously maintained with elaborate means—in the course of the passage of the femtosecond laser pulse, in such a manner that the focusability of the femtosecond laser radiation suffers considerably thereby, and under certain circumstances no laser-induced optical breakdown and/or no plasma arises in the cornea, in which case the LASIK incision consequently does not succeed or succeeds only in a poorer quality or has to be produced with a considerably higher femtosecond-pulse energy.

The optical contact element gives rise to the wavefront error of at most about λ/2, preferentially at most about, λ/4, highly preferentially at most about λ/10, within a wavelength range of the light beam, traversing it from about 1000 nm to about 1200 nm. A typical femtosecond laser source generates laser pulses with a wavelength of about 1035 nm±10 nm, for example. In one embodiment the optical eye-contact element has to exhibit the low wavefront error at least within thin range, it being possible for an approximately double wavefront error to result at a wavelength of about 520 nm.

The optical eye-contact element may exhibit a refractive index $\eta_1$ from about 1.35 to about 1.40, preferentially from about 1.36 to 1.38, highly preferentially about 1.37. The refractive index $\eta_2$ of the cornea amounts, to about 1.37, and if the refractive index of the optical eye-contact element exhibits a similar refractive index the quality and/or the intensity of a light beam or laser beam at the transition from the optical eye-contact element into the cornea is/are not diminished.

The reflection losses R are computed as follows:

$$R = \left(\frac{\eta_2 - \eta_1}{\eta_2 + \eta_1}\right)^2$$

When $\eta_2 \approx \eta_1$ it follows that almost no reflection losses occur.

The optical eye-contact element may be biocompatible. Biocompatible materials do not have any negative influence in the eye. The optical eye-contact element may exhibit a biocompatible layer on the region that, in use, comes into contact with the eye. The biocompatible layer may exhibit proteins, for example.

The optical contact element may exhibit a high stability in relation to femtosecond laser pulses. This is important, in so particular, on account of the high energy density of the laser pulses. The high stability in relation to high radiation intensities (high damage threshold)—for example, in relation to femtosecond laser pulses—may be obtained, for example, by means of a high transmission of the optical eye-contact element. The optical eye-contact element may, for example, exhibit glass of type BK7. A glass of type BK7 with a thickness of 10 mm may exhibit a transmission of more than about 90% within a wavelength range from about 370 nm to about 1700 nm, with a higher transmission arising in the case of a lower thickness of the glass. The optical eye-contact element may also exhibit quarts glass (fused silica).

The optical eye-contact element may exhibit an optical plastic. As a result, the optical eye-contact element becomes relatively inexpensive, despite its high quality.

A further aspect of the invention relates to a femtosecond laser system that includes a femtosecond laser source and the eye-contact element described above. The femtosecond laser system may further include a scanner, with at least one deflecting mirror for positioning the femtosecond laser beam at a treatment site on the eye of a patient, and focusing optics for focusing the femtosecond laser beam.

Figure 2:
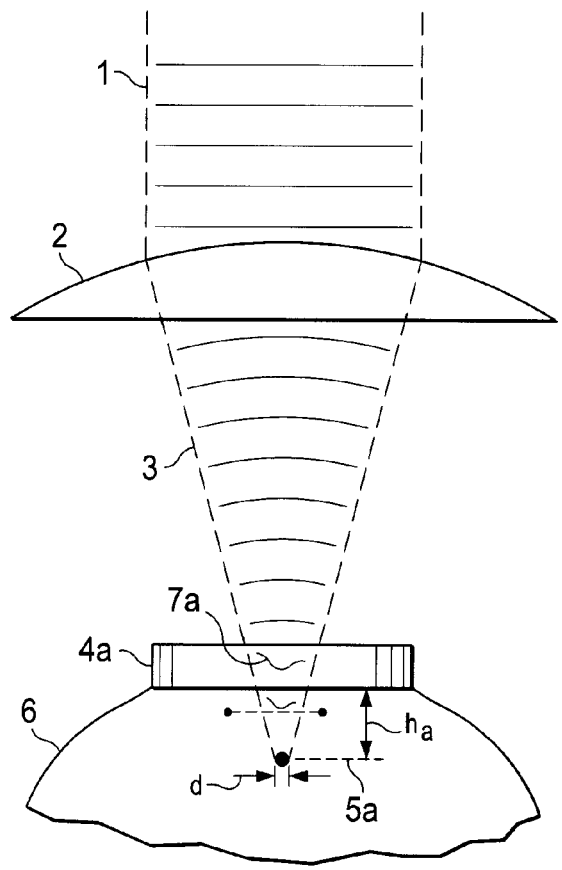
Figure 3:
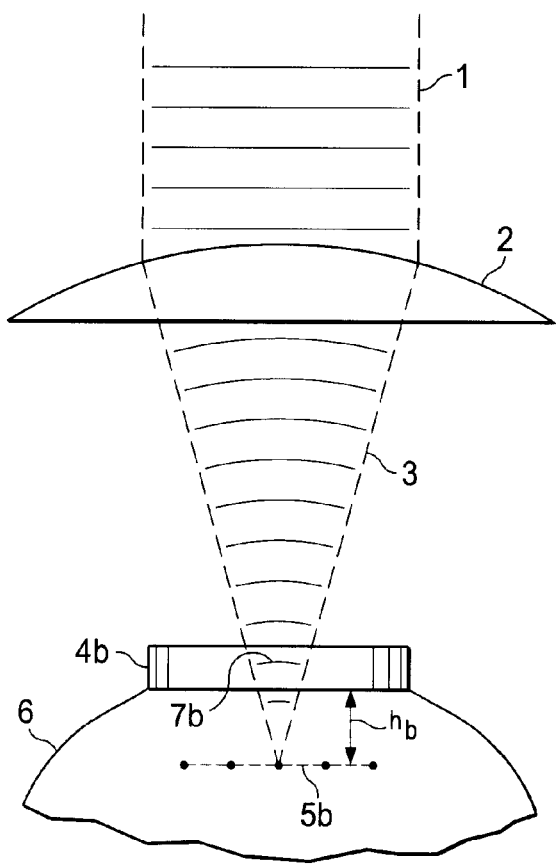

The invention will now be described in more detail with reference to the accompanying drawings, wherein FIG. 1 is a schematic, greatly simplified view of a femtosecond microkeratome, FIG. 2 shows the location and the diameter of the regions of focus in the case of a conventional optical eye-contact element, and FIG. 3 shows the location and the diameter of the regions of focus in the case of an optical eye-contact element according to the invention.

FIG. 1 shows a femtosecond microkeratome with a femtosecond laser source 10 which generates a femtosecond laser beam 11 with a low wavefront error. The femtosecond laser beam 11 is deflected by means of a first deflecting mirror 12 and a second deflecting mirror 14 of an optical scanner, so that an arbitrary point in the treatment region on the cornea 6 of a patient's eye 18 can be reached. The femtosecond laser beam 11 deflected by the first deflecting mirror 12 and by the second deflecting mirror 14 is focused by focusing optics 16 and enters an optical contact element 4b according to the invention. The optical eye-contact element 4b according to the invention applanates the cornea 6. As a result, a defined spacing between the focusing optics 16 and the cornea 6 can be maintained. Upon emergence of the femtosecond laser beam 11 from the optical contact element, a laser-induced optical breakdown arises approximately in the region of focus of the femtosecond laser beam 11, i.e. approximately in the plane of the focal length of the focusing objective 16. By a plurality of femtosecond laser beams 11 being directed successively over the treatment region in the cornea 6, a planar incision arises inside the cornea 6 of the eye 18.

FIG. 2 shows the progression of the wave in the case of a conventional eye-contact element 4a. A femtosecond laser beam 1 of very high quality is directed towards a focusing lens 2 of good quality which, for example, gives rise to a wavefront error of $\lambda/10$. The focusing lens 2 bundles the incident femtosecond laser beam 1 into a focused femtosecond laser beam 3 which still exhibits a high quality. Within the context, of this invention, high quality of a laser beam signifies a small wavefront error. The focused femtosecond laser beam strikes a conventional eye-contact element 4a, for example an applanation plate or applanation lens. Conventional eye-contact elements give rise to a wavefront error of, for example, $2.2\lambda$. By reason of the low optical quality of the conventional eye-contact element, a wavefront error 7a arises. The diameter of the regions of focus 5a resulting from the focused femtosecond laser beam 3 is therefore significantly larger than the theoretical diameter that can be obtained on the basis of the Airy function. Furthermore, by reason of the wavefront errors arising in the conventional eye-contact element, the regions of focus 5a are located at varying and/or non-uniform depths of focus $h_a$.

By reason of the relatively large diameter of the regions of focus 5a, a higher laser-pulse energy is required in order to obtain the laser-induced optical breakdown for an incision in the cornea. Furthermore, the optimal result of treatment—i.e. quality of incision—is not achieved, since the regions of focus 5a are located at a varying and/or non-uniform depth $h_a$, and therefore a femtosecond laser incision arises having great roughness.

FIG. 3 shows a wavefront error in the case of an optical eye-contact element according to the invention. FIG. 3 resembles FIG. 2, and similar components and elements in the Figures are labelled with the same reference symbols.

The femtosecond laser beam 1 of high quality, i.e. with a low wavefront error, is bundled by means of a focusing lens 2, which gives rise to a wavefront error of about $\lambda/10$, into a focused femtosecond laser beam 3 with a low wavefront error. The focused femtosecond laser beam 3 traverses an optical eye-contact element 4b which gives rise to a wavefront error of at most about $\lambda/2$, preferentially at most about $\lambda/4$, highly preferentially at most about $\lambda/10$. By reason of the low wavefront error caused by the optical eye-contact element 4b according to the invention, the wavefronts 7b have, moreover, a high quality. The regions of focus in the corneal resulting from the focused femtosecond laser beam 3 therefore exhibit almost the minimal diameter that results from the Airy function. Furthermore, the regions of focus are located at an almost constant depth $h_b$ in the cornea 6, and the roughness of the incision is slight.

Simulations have shown that in the case of a femtosecond laser beam with a wavelength of 1035 nm±2.5 nm and in the case of a conventional optical eye-contact element, which gives rise to a wavefront error of $2.2\lambda$, a radius of the region of focus of $\geq 30$ μm arises. In air, the centre of the regions of focus would be located at a distance of 220 μm from the boundary surface between the optical eye-contact element and the air. In the case of a conventional optical eye-contact element, a wavefront error PV (peak-valley) in the focal plane of $1.14\lambda$ arises.

Under the same conditions, in the case of an ideal optical eye-contact element, which gives rise to a wavefront error of $0\lambda$, a radius of $\leq 15$ μm for the region of focus arises. In air, the centre of the region of focus would be situated at a distance of 380 μm from the boundary surface between the optical eye-contact element and the air. A wavefront error PV of the laser beam of only $0.62\lambda$ arises in the region of focus.

In the above simulation the eye-contact element 4b according to the invention exhibited a thickness of 7 mm and was formed from a plane-parallel plate with the material BK7. The input beam had a diameter of 15 mm with a Gaussian plane wave. The field of treatment had a diameter of 6 mm. The focusing objective comprised two diverging lenses and one focusing lens. No manufacturing tolerances and no aspherical surfaces of the focusing objectives were taken into account. The focal length of the objective in air amounted to 38 mm, starting from the last principal plane.

The simulation represents merely a crude demonstration of the influence of the wavefront quality of the optical contact element. In real systems with a precise focusing objective, i.e. not with a simple objective with three lenses as in the case of the present simple simulation, the influence of the average wave-front quality of the optical contact element is clearly greater, since focal diameters of $d_F \approx 5$ μm are in fact obtained with the best optical devices. The result of the influence of a non-optimised applanation plate would foe distinctly poorer with a focal diameter of $d_F > 30$. In the case where use is made of an optical contact element with a good wave-front-error correction, the scan field—which in practice is larger—of about 10 mm to 12 mm also has a strong tendency to increase the differences in comparison with an optical contact element with a poor wavefront-error correction.

The invention has the advantage that the diameter of the regions of focus exhibits almost the minimal theoretical possible value, as a result of which merely a lower femtosecond-pulse energy is required for the purpose of producing a laser-induced optical breakthrough. Furthermore, the optical eye-contact element according to the invention enables incisions of higher quality, since the midpoint of the regions of focus is located at a defined distance from the optical eye-contact element.

The invention claimed is:

1. A method of performing ophthalmic surgery, comprising:
    providing a laser system including:
        a laser source configured to generate a femtosecond laser beam having a wavelength between about 1000 nm and about 1200 nm; and
        a focusing lens in optical communication with the laser source, the focusing lens configured to focus the femtosecond laser beam into a focused femtosecond laser beam;
    providing an applanation lens having a planar surface configured to applanate an eye to be treated, the applanation lens having a transmission rate of at least 90% relative to the focused femtosecond laser beam and configured to introduce a wavefront error of at most about $\lambda/10$ to the focused femtosecond laser beam when the focused femtosecond laser beam passes through the applanation lens;
    positioning the applanation lens against the eye to be treated to applanate the eye;
    directing the focused femtosecond laser beam through the applanation lens and onto the eye, the applanation lens introducing a wavefront error of at most about $\lambda/10$ to the focused femtosecond laser beam such that the focused femtosecond laser beam has a region of focus within a cornea of the eye, the region of focus having a diameter of 15 μm or less; and
    repeating the directing step to successively direct the focused femtosecond laser beam having the region of focus with a diameter of 15 μm or less over a treatment region within the cornea of the eye to form an incision in the cornea.

2. The method of claim 1, wherein the provided applanation lens has a refractive index between about 1.35 and about 1.40 relative to the focused femtosecond laser beam.

3. The method of claim 1, wherein the provided applanation lens is formed from a material selecting from the group of materials consisting of BK7 glass, quartz glass, and optical plastic.

4. The method of claim 1, wherein the provided applanation lens is a plane-parallel plate.

5. The method of claim 1, wherein the provided applanation lens has a thickness of approximately 7 mm.

6. The method of claim 1, wherein the focusing lens of the provided laser system introduces a wavefront error of at most about $\lambda/10$ to the femtosecond laser beam.

7. The method of claim 1, wherein repeating the directing step results in the incision being planar.

8. The method of claim 1, wherein repeating the directing step results in the region of focus of the focused femtosecond laser beam having a substantially constant depth.

9. The method of claim 8, wherein the resulting incision has a substantially constant depth.

10. A method of performing ophthalmic surgery, comprising:
    providing an applanation lens having a planar surface configured to applanate an eye to be treated, the applanation lens having a transmission rate of at least 90% relative to a focused femtosecond laser beam having a wavelength between about 1000 nm and about 1200 nm and configured to introduce a wavefront error of at most about $\lambda/2$ to the focused femtosecond laser beam when the focused femtosecond laser beam passes through the applanation lens;
    positioning the applanation lens against the eye to be treated to applanate the eye;
    directing a focused femtosecond laser beam having a wavelength between about 1000 nm and about 1200 nm through the applanation lens and onto the eye, the applanation lens introducing a wavefront error of at most about $\lambda/2$ to the focused femtosecond laser beam such that the focused femtosecond laser beam has a region of focus within a cornea of the eye, the region of focus having a diameter of 15 μm or less; and
    repeating the directing step to successively direct the focused femtosecond laser beam having the region of focus with a diameter of 15 μm or less over a treatment region within the cornea of the eye to form an incision in the cornea.

11. The method of claim 10, wherein the provided applanation lens has a refractive index between about 1.35 and about 1.40 relative to the focused femtosecond laser beam.

12. The method of claim 10, wherein the provided applanation lens is formed from a material selecting from the group of materials consisting of BK7 glass, quartz glass, and optical plastic.

13. The method of claim 10, wherein the provided applanation lens is a plane-parallel plate.

14. The method of claim 10, wherein the provided applanation lens has a thickness of approximately 7 mm.

15. The method of claim 10, wherein the provided applanation lens is configured to introduce a wavefront error of at most about $\lambda/4$ to the focused femtosecond laser beam when the focused femtosecond laser beam passes through the applanation lens and wherein the applanation lens introduces a wavefront error of at most about $\lambda/4$ to the focused femtosecond laser beam when the focused femtosecond laser beam is directed through the applanation lens and onto the eye.

16. The method of claim 10, wherein the provided applanation lens is configured to introduce a wavefront error of at most about $\lambda/10$ to the focused femtosecond laser beam when the focused femtosecond laser beam passes through the applanation lens and wherein the applanation lens introduces a wavefront error of at most about $\lambda/10$ to the focused femtosecond laser beam when the focused femtosecond laser beam is directed through the applanation lens and onto the eye.

17. The method of claim 10, wherein repeating the directing step results in the incision being planar.

18. The method of claim 10, further comprising:
    providing a laser system including:
        a laser source configured to generate a femtosecond laser beam having a wavelength between about 1000 nm and about 1200 nm; and
        a focusing lens in optical communication with the laser source, the focusing lens configured to focus the femtosecond laser beam into the focused femtosecond laser beam.

19. The method of claim 18, wherein the focusing lens of the provided laser system introduces a wavefront error of at most about $\lambda/10$ to the femtosecond laser beam.

20. The method of claim 10, wherein repeating the directing step results in the region of focus of the focused femtosecond laser beam having a substantially constant depth such that the incision has a substantially constant depth.

* * * * *